(12) United States Patent
May et al.

(10) Patent No.: US 6,656,358 B2
(45) Date of Patent: Dec. 2, 2003

(54) METHOD FOR THE CHROMATOGRAPHIC ISOLATION OF VITAMIN E ISOMERS

(75) Inventors: Choo Yuen May, Kajang (MY); Ma Ah Ngan, Kajang (MY); Yusof Basiron, Kajang (MY)

(73) Assignee: Malaysian Palm Oil Board, Kajang (MY)

( * ) Notice: Subject to any disclaimer, the term of this patent is extended or adjusted under 35 U.S.C. 154(b) by 151 days.

(21) Appl. No.: 09/773,573

(22) Filed: Feb. 2, 2001

(65) Prior Publication Data

US 2001/0044548 A1 Nov. 22, 2001

(30) Foreign Application Priority Data

Feb. 2, 2000 (MY) ...................................... PI 20000368

(51) Int. Cl.[7] .............................................. B01D 15/08
(52) U.S. Cl. ...................... 210/635; 210/656; 210/659; 210/634; 549/413; 554/174
(58) Field of Search ........................ 549/413; 554/174; 210/635, 656, 659, 198.2, 634

(56) References Cited

U.S. PATENT DOCUMENTS

| | | | |
|---|---|---|---|
| 4,122,094 A | 10/1978 | Woziwodzki | 260/345.6 |
| 4,964,995 A * | 10/1990 | Chum | 210/634 |
| 5,157,132 A | 10/1992 | Tan et al. | 549/413 |
| 5,190,618 A | 3/1993 | Top et al. | 203/34 |
| 5,866,004 A * | 2/1999 | Houck | 210/634 |
| 5,908,940 A * | 6/1999 | Lane | 549/413 |
| 5,972,357 A * | 10/1999 | Yamaguchi | 424/401 |
| 6,395,915 B1 * | 5/2002 | Bellafiore | 554/193 |

FOREIGN PATENT DOCUMENTS

| | | | |
|---|---|---|---|
| EP | 1 122 250 | 8/2001 | |
| GB | 2 218 989 A | 11/1989 | 210/656 |

OTHER PUBLICATIONS

Ibanez, E. et al., "Isolation and Separation of Tocopherols from Olive By–products with Supercritical Fluids," JAOCS 77:2, pp. 187–190, 2000.

Grezgorz Galuba, et al., "Separation of Tocopherols and Sterols in Soybean Oil Condensate Utilizing Supercritical Fluid Chromatography (SFC)," Chem. Anal. 42, pp. 245–248, 1997.

A. Staby et al., "Quantitative Analysis of Marine Oils by Capillary Supercritical Fluid Chromatography," Chromatographia 39:11/12, pp. 697–705, 1994.

Takashi Yarita et al., "Supercritical Fluid Chromatographic Determination of Tocopherols on an ODS–silica gel column," Journal of Chromatography 679, pp. 329–334, 1994.

Abstract of JP21 57274, Dec. 7, 1998 (1 page).

* cited by examiner

*Primary Examiner*—Ernest G. Therkorn
(74) *Attorney, Agent, or Firm*—Pennie & Edmonds LLP

(57) ABSTRACT

A method for the chromatographic separation of vitamin E isomers such as α-tocopherol, β-tocopherol, γ-tocopherol, δ-tocopherol, α-tocotrienol, β-tocotrienol, γ-tocotrienol and δ-tocotrienol from a vitamin E containing mixture by combining the vitamin E mixture with an adsorbent to effect adsorption of the vitamin E isomers on the adsorbent; and then selectively desorbing the vitamin E isomers from the adsorbent with a solvent under supercritical conditions.

22 Claims, No Drawings

METHOD FOR THE CHROMATOGRAPHIC ISOLATION OF VITAMIN E ISOMERS

FIELD OF THE INVENTION

The invention relates to methods for the chromatographic isolation of vitamin E isomers. In particular to methods of isolating individual vitamin E isomers such as α-tocopherol, β-tocopherol, γ-tocopherol, δ-tocopherol, α-tocotrienol, α-tocotrienol, γ-tocotrienol, δ-tocotrienol and the like from vitamin E containing mixtures such as crude palm oil, palm oil products, palm oil by-products, vegetable oils, and the like.

BACKGROUND OF THE INVENTION

Tocols are vitamin E compounds that include tocopherols (T) and tocotrienols ($T_3$) that are found in vegetable oils in varying quantities (See, e.g., Table A). The tocols present in most vegetable oils are typically in the form of tocopherols (α-, β-, γ-, and δ-tocopherols). Palm oil, however, is unique since the tocols are present mainly in the form of tocotrienols (α-$T_3$, γ-$T_3$, and δ-$T_3$). Each of the tocols exhibits interesting physiological properties.

TABLE A

| Tocopherols Amounts in Vegetable Oils (mg/kg) | | | | | | |
|---|---|---|---|---|---|---|
| Oil | δ-T | β-T | γ-T | δ-T | α$T_3$ | γ-T3 | δ-$T_3$ |
| Castor | 28 | 29 | 111 | 310 | — | — | — |
| Cocoa butter | 11 | — | 170 | 17 | 2 | — | — |
| Coconut | — | — | — | 2–4 | 20 | — | — |
| Corn | 134 | 18 | 412 | 39 | — | — | — |
| Cottonseed | 573 | 40 | 317 | 10 | — | — | — |
| Groundnut | 169 | 5 | 144 | 13 | — | — | — |
| Linseed | — | — | — | — | — | — | — |
| Mustard | 75 | — | 494 | 31 | — | — | — |
| Olive | 93 | — | 7 | — | — | — | — |
| Palm from fibers | 1662 | — | — | — | 456 | 485 | 142 |
| Palm | 150 | — | — | — | 1127 | 297 | 80 |
| Palm | 279 | — | 61 | — | 274 | 398 | 69 |
| Rape | 70 | 16 | 178 | 7 | — | — | — |
| Rice bran | 324 | 18 | 53 | — | 236 | 349 | — |
| Safflower | 477 | — | 44 | 10 | — | — | — |
| Sesame | 12 | 6 | 244 | 32 | — | — | — |
| Soyabean | 116 | 34 | 737 | 275 | — | — | — |
| Sunflower | 608 | 17 | 11 | — | — | — | — |
| Wheat germ | 1179 | 398 | 493 | 118 | tr | — | — |

Both tocopherols and tocotrienols act as powerful nutritional antioxidants and help to reduce cellular damage due to free radicals arising from the body's normal oxidative energy metabolism or from the action of toxic chemicals and pollutants in our environment. Free radicals have been implicated in aging, chronic degenerative diseases, and cancer.

Vitamin E is also a natural antioxidant, present at approximately 600–1000 ppm in crude palm oil; the major component being γ-tocotrienol. Recently it has been reported that γ-tocotrienol has anti-cancer properties in addition to its known antioxidant activity. Tocotrienols have been found to lower blood cholesterol.

U.S. Pat. No. 5,190,618 discloses a process for extracting vitamin E from palm fatty acid distillates (PFAD). The process involves converting the PFAD into methyl esters and distilling the methyl esters followed by ion-exchange chromatography and molecular distillation to get a vitamin E concentrate of more than 90%.

U.S. Pat. No. 5,157,132 discloses a process for extracting vitamin E from crude palm oil (CPO) by converting the CPO to methyl esters and then removing the esters by molecular distillation to yield carotene-rich and vitamin E-rich fractions.

GB 2,218,989 discloses converting crude palm oil into methyl esters followed by chromatographic separation of the methyl esters, on an adsorbent in the presence of solvents, to yield carotene-rich, vitamin E-rich, and sterol-rich fractions.

These patents only describe the isolation of vitamin E-rich fractions from palm oil and do not disclose the isolation individual vitamin E isomers which may exhibit important physiological properties. Thus, all of the previously known methods that involve in the adsorption/desorption chromatographic separation only isolate mixtures of vitamin E isomers rather than individual isomers. Moreover, these methods all use solvents that are costly and hazardous.

There is a need for methods to separate and isolate vitamin E isomers that avoids or eliminates the sole use of solvents and consequently, renders the process "non-hazardous."

SUMMARY OF THE INVENTION

The invention relates to a method for the chromatographic separation of vitamin E isomers from a vitamin E containing mixture. The method involves the steps of combining the vitamin E mixture with an adsorbent to effect adsorption of the vitamin E isomers on the adsorbent and selectively desorbing the vitamin E isomers from the adsorbent with a solvent under supercritical conditions.

The vitamin E isomers may be one or more of α-tocopherol, β-tocopherol, γ-tocopherol, δ-tocopherol, α-tocotrienol, β-tocotrienol, γ-tocotrienol and δ-tocotrienol. The adsorbent may be silica gel, reverse phase C-18 silica gel, or a mixtures thereof. The solvent may be $CO_2$, propane, propene, or ethylene. Preferably, the solvent is $CO_2$. The solvent may optionally further include an entrainer such as an alcohol. In one embodiment the separation is performed at a temperature of about 20° C. to 150° C. and a pressures of about 20 kg/cm² to 800 kg/cm². The vitamin E containing mixture may be crude palm oil, palm oil products, palm oil by-products, vegetable oils, and a vitamin E concentrate.

When the vitamin E containing mixture is a vitamin E concentrate the vitamin E concentrate may be formed by esterifying free fatty acid components of the vitamin E containing mixture with one or more monohydric alcohols to provide esters followed by removing the esters to form the vitamin E concentrate, or by trans-esterifying glyceride components the vitamin E containing mixture with one or more monohydric alcohols to provide esters and then removing the esters to form the vitamin E concentrate. The alcohol may be a $C_1$ to $C_8$ alcohol, such as methanol.

The free fatty acid components of the vitamin E containing mixture may be esterified using a catalyst selected from the group consisting of a solid alkali metal bisulfate acid, a solid alkali metal sulfate acid, a strongly acidic ion exchange resin, and an enzyme. The glyceride components of the vitamin E containing mixture may be trans-esterifed using a basic catalyst or an enzyme.

DETAILED DESCRIPTION OF THE PREFERRED EMBODIMENTS

The present invention provides a method for the chromatographic separation of vitamin E isomers from vitamin E containing mixtures.

The phrase "vitamin E containing mixtures," as used herein, means any mixture or combination of compounds that includes vitamin E. Preferably, the vitamin E containing mixture is one or more of crude palm oil (CPO), palm oil products, palm oil by-products, or other vegetable oils and fats. More preferably, the vitamin E containing mixture is one or more of crude palm oil.

In particular the present invention uses a supercritical fluid (such as SC—$CO_2$) in combination with one or more adsorbents to effect adsorption and desorption of the vitamin E isomers resulting in the vitamin E isomers being separated from the other compounds in the vitamin E containing mixture. Preferably, the individual vitamin E isomers are also separated from each other.

In one embodiment the present invention involves isolating vitamin E isomers from a vitamin E concentrate. The phrase "vitamin E concentrate," as used herein means a vitamin E containing mixture that has been treated chemically and/or physically to increase the concentration of vitamin E. Preferably, the vitamin E concentrate may be prepared, for example, a. from crude vegetable oil esters via catalytic alcoholic esterification/transesterification of the vegetable oils and distilling the esters to yield the vitamin E concentrate; or b. from unsaponifiable matters of vegetable oils and fats by a saponification process;

c. by any process, such as chromatography (solvent and supercritical) and supercritical fluid extraction.

An important feature of the invention is that liquefied gas at supercritical conditions is used in the separation. Using a supercritical fluid avoids or reduces the prior requirements for hazardous solvents. To date, there has not been disclosed any method that uses a supercritical fluid for the adsorption/desorption chromatographic isolation/separation of Vitamin E isomers from plant sources such as crude palm oil, palm oil products, palm oil by-products, and other vegetable oils and fats.

The method of the invention for the chromatographic isolation of vitamin E isomers from crude palm oil, palm oil products, palm oil by-products, vegetable oils and vitamin E containing mixtures involves combining the vitamin E containing mixtures with an adsorbent to effect adsorption of vitamin E isomers on the adsorbent and selectively desorbing the vitamin E isomers from the adsorbent, wherein the adsorption/desorption of the vitamin E isomers is carried in a supercritical fluid environment.

In one embodiment the separation is applied to a vitamin E concentrate from the vitamin E containing mixture. The vitamin E concentrate may be obtained, for example, by:

(a) Esterifying the free fatty acid component of the vitamin E containing mixture with one or more monohydric alcohols to provide esters and then removing the resulting esters by vacuum distillation or molecular distillation to provide the vitamin E concentrate. The esters may be removed via vacuum distillation or molecular distillation. The esterification may be carried out with a solid alkali metal bisulfate or sulfate acid, strongly acidic-ion exchange resin, or any effective acid as a catalyst; or (b) Trans-esterifying the glyceride components of a vitamin E containing mixture with one or more monohydric alcohols, preferably $C_1$ to $C_8$ alcohols, to provide monoesters and then removing the resulting monoesters by vacuum distillation or molecular distillation to provide the vitamin E concentrate. The monoesters may be removed via vacuum distillation or molecular distillation. The trans-esterification may be carried out with a basic catalyst.

Alternatively, steps a and b may be carried out with an enzyme (e.g., *candida rugosa*) as a catalyst.

(c) Supercritical chromatography and/or any other chromatographic method which is effective in extracting a vitamin E concentrate from vegetable oils.

The present invention may also be applied to unsaponifiable materials as obtained by the saponification of vegetable oils.

Suitable adsorbent for the adsorption of the Vitamin E isomers include, but are not limited to, silica gel, C-18 reverse phase silica gel, and the like which are effective in adsorbing vitamin E isomers from vitamin E containing mixtures. One of ordinary skill in the art will readily be able to select suitable adsorbents for use in the methods of the invention.

Suitable solvents for use in the methods of the invention include supercritical fluid such as $CO_2$, (SC—$CO_2$), propane, propene, ethylene and the like. Preferably the supercritical fluid is $CO_2$. The supercritical fluid may also be a supercritical fluid, such as SC—$CO_2$ in combination with an entrainer. Suitable entrainers for use in the method of the invention include alcohols and organic solvents.

Typical operating conditions for the methods of the invention include pressures from about 20 kg/cm$^2$ to 800 kg/cm$^2$, preferably from about 50 kg/cm$^2$ to 600 kg/cm$^2$ and temperatures from about 20° C. to 150° C., preferably, temperatures from about 30° C. to 100° C. Individual Vitamin E isomers may be isolated with substantially higher purity (e.g., >50%) in a single run under these conditions.

The Vitamin E isomers recovered by the methods of the invention are useful in pharmaceutical compositions, food and health food formulations, dietary supplements, and cosmetics formulations. They can also be used as fine chemicals and standard reference materials.

EXAMPLES

The invention is further defined by reference to the following examples describing in detail the methods of the present invention. The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The following examples illustrate that supercritical fluid applied to solid adsorbents (silica gel and/or C18 reverse phase silica gel) provides a satisfactory means for isolating Vitamin E isomers ($\alpha$-T, $\beta$-T, $\gamma$-T, $\delta$-T and $\alpha$-$T_3$, $\beta$-$T_3$, $\gamma$-$T_3$ and $\delta$-$T_3$) from crude palm oil, palm oil products, vegetable oil and other vitamin E containing mixtures. In the tables that follow "T" means tocopherol, "$T_3$" means tocotrienol, and "S/M" means starting material.

Example 1

Isolation of Palm Vitamin E Isomers

Crude palm oil, containing 600 to 1000 ppm of vitamin E, was transesterified into methyl esters. The methyl esters were removed by molecular distillation at a temperature of between 90 to 180° C. to yield a vitamin E concentrate (>50%). The vitamin E concentrate (0.01 g; concentration≈50%) was dissolved in an organic solvent, such as dichloromethane or ethanol, and loaded onto a column containing silica gel. The column had an internal diameter of 20 mm and a length of 250 mm). The vitamin E concentrate was eluted with a mixture of supercritical carbon dioxide (5 mL, 95.2%) and an entrainer, ethanol (0.25 mL, 4.8%), at a flow rate of 5.25 mL/min. The pressure of the supercritical fluid chromatography system was maintained at a pressure of 180 kg/cm$^2$, and the temperature was maintained at 70° C. Four vitamin E isomers were collected at different time intervals and are shown in Table 1. The presence and concentration of vitamin E isomers was confirmed by HPLC.

TABLE 1

Isolation of Vitamin E Isomers From Crude Palm Oil
($\alpha$-T, $\alpha$-T$_3$, $\gamma$-T$_3$ and $\delta$-T$_3$)

| Fractions | Collection Time (mm) | Vit. E $\alpha$-T | Vit. E $\alpha$-T$_3$ | Vit. E $\gamma$-T$_3$ | Vit. E $\delta$-T$_3$ |
|---|---|---|---|---|---|
| S/M | — | 12.7 | 11.4 | 19 | 5.8 |
| 1 | — | — | — | — | — |
| 2 | 41–47 | 100 | — | — | — |
| 3 | 47–54 | — | 100 | — | — |
| 4 | 54–61 | — | — | 100 | — |
| 5 | 61–77 | — | — | 99 | 1 |
| 6 | 77–145 | — | — | 3 | 97 |
| 7 | 145– | — | — | — | — |

Example 2

The procedure of Example 1 was repeated except that the vitamin E concentrate (≈90%) was obtained from palm fatty acid distillate. The results are shown in Table 2.

TABLE 2

Isolation of Vitamin E Isomers from Palm Fatty Acid Distillate
($\alpha$-T, $\alpha$-T$_3$, $\gamma$-T$_3$ and $\delta$-T$_3$)

| Fractions | Collection Time (mm) | Vit. E $\alpha$-T | Vit. E $\alpha$-T$_3$ | Vit. E $\gamma$-T$_3$ | Vit. E $\delta$-T$_3$ |
|---|---|---|---|---|---|
| S/M | — | 22.7 | 21.4 | 39 | 9.8 |
| 1 | — | — | — | — | — |
| 2 | 41–47 | 100 | — | — | — |
| 3 | 47–54 | — | 100 | — | — |
| 4 | 54–61 | — | — | 100 | — |
| 5 | 61–77 | — | — | 99 | 1 |
| 6 | 77–145 | — | — | 2 | 98 |
| 7 | 145– | — | — | — | — |

Example 3

The procedure of example 1 was repeated except the vitamin E concentrate (≈90%) was obtained from palm pressed fiber oil. The results are shown in Table 3.

TABLE 3

Isolation of Vitamin E Isomers from Palm Pressed Fibre Oil
($\alpha$-T, $\alpha$-T$_3$, $\gamma$-T$_3$ and $\delta$-T$_3$)

| Fractions | Collection Time (mm) | Vit. E $\alpha$-T | Vit. E $\alpha$-T$_3$ | Vit. E $\gamma$-T$_3$ | Vit. E $\delta$-T$_3$ |
|---|---|---|---|---|---|
| S/M | — | 42.7 | 11.4 | 29 | 10.8 |
| 1 | — | — | — | — | — |
| 2 | 41–47 | 100 | — | — | — |
| 3 | 47–54 | — | 100 | — | — |
| 4 | 54–61 | — | — | 100 | — |

TABLE 3-continued

Isolation of Vitamin E Isomers from Palm Pressed Fibre Oil
($\alpha$-T, $\alpha$-T$_3$, $\gamma$-T$_3$ and $\delta$-T$_3$)

| Fractions | Collection Time (mm) | Vit. E $\alpha$-T | Vit. E $\alpha$-T$_3$ | Vit. E $\gamma$-T$_3$ | Vit. E $\delta$-T$_3$ |
|---|---|---|---|---|---|
| 5 | 61–77 | — | — | 99 | 1 |
| 6 | 77–145 | — | — | 2.2 | 97.8 |
| 7 | 145– | — | — | — | — |

Example 4

The procedure of example 1 was repeated except that a soybean oil vitamin E concentrate (≈80%) was used. The results are shown in Table 4.

TABLE 4

Isolation of Vitamin E Isomers ($\alpha$-T, $\beta$-T, $\gamma$-T and $\delta$-T)
from Soyabean Oil

| Fractions | Collection Time (mm) | Vit. E $\alpha$-T | Vit. E $\alpha$-T$_3$ | Vit. E $\gamma$-T$_3$ | Vit. E $\delta$-T$_3$ |
|---|---|---|---|---|---|
| S/M | — | 11.6 | 3.4 | 53.7 | 17.5 |
| 1 | — | — | — | — | — |
| 2 | 35–41 | 100 | — | — | — |
| 3 | 42–47 | — | 99 | — | — |
| 4 | 48–55 | — | — | 100 | — |
| 5 | 58–65 | — | — | — | 100 |

Example 5

The procedure of example 1 was repeated except that a corn oil vitamin E concentrate (≈80%) was used. The results are shown in Table 5.

TABLE 5

Isolation of Vitamin E Isomers ($\alpha$-T, $\beta$-T, $\gamma$-T and $\delta$-T)
from Corn Oil

| Fractions | Collection Time (mm) | Vit. E $\alpha$-T | Vit. E $\alpha$-T$_3$ | Vit. E $\gamma$-T$_3$ | Vit. E $\delta$-T$_3$ |
|---|---|---|---|---|---|
| S/M | — | 23.4 | 1.8 | 51.2 | 3.9 |
| 1 | — | — | — | — | — |
| 2 | 35–41 | 100 | — | — | — |
| 3 | 42–47 | — | 92 | — | — |
| 4 | 48–55 | — | — | 100 | — |
| 5 | 58–65 | — | — | — | 92 |

Example 6

The procedure of example 1 was repeated except that a vitamin E concentrate (≈90%) from Canola (rapeseed oil) oil was used. The results are shown in Table 6.

TABLE 6

Isolation of Vitamin E Isomers ($\alpha$-T, $\beta$-T, $\gamma$-T and $\delta$-T)
from Canola Oil

| Fractions | Collection Time (mm) | Vit. E $\alpha$-T | Vit. E $\alpha$-T$_3$ | Vit. E $\gamma$-T$_3$ | Vit. E $\delta$-T$_3$ |
|---|---|---|---|---|---|
| S/M | — | 20 | 8 | 58 | 2 |
| 1 | — | — | — | — | — |
| 2 | 35–41 | 100 | — | — | — |

TABLE 6-continued

Isolation of Vitamin E Isomers (α-T, β-T, γ-T and δ-T) from Canola Oil

| Fractions | Collection Time (mm) | Vit. E α-T | Vit. E α-T$_3$ | Vit. E γ-T$_3$ | Vit. E δ-T$_3$ |
|---|---|---|---|---|---|
| 3 | 42–47 | — | 85 | — | — |
| 4 | 48–55 | — | — | 100 | — |
| 5 | 58–65 | — | — | — | 80 |

Example 7

The procedure of example 1 was repeated except that a vitamin E concentrate (≈90%) from olive oil was used. The results are shown in Table 7.

TABLE 7

Isolation of Vitamin E Isomers (α-T, β-T, γ-T and δ-T) from Olive Oil

| Fractions | Collection Time (mm) | Vit. E α-T | Vit. E α-T$_3$ | Vit. E γ-T$_3$ | Vit. E δ-T$_3$ |
|---|---|---|---|---|---|
| S/M | — | 83 | 7 | — | — |
| 1 | — | — | — | — | — |
| 2 | 35–41 | 100 | — | — | — |
| 3 | 42–47 | — | 80 | — | — |
| 4 | 48–55 | — | — | — | — |
| 5 | 58–65 | — | — | — | — |

Example 8

The procedure of example 1 was repeated except that a vitamin E concentrate (≈90%) from cottonseed oil was used. The results are shown in Table 8.

TABLE 8

Isolation of Vitamin E Isomers (α-T, β-T, γ-T and δ-T) from Cottonseed Oil

| Fractions | Collection Time (mm) | Vit. E α-T | Vit. E α-T$_3$ | Vit. E γ-T$_3$ | Vit. E δ-T$_3$ |
|---|---|---|---|---|---|
| S/M | — | 57.3 | 4 | 31.7 | 1 |
| 1 | — | — | — | — | — |
| 2 | 35–41 | 100 | — | — | — |
| 3 | 42–47 | — | 92 | — | — |
| 4 | 48–55 | — | — | 100 | — |
| 5 | 58–65 | — | — | — | 85 |

Example 9

The procedure of example 1 was repeated except that a vitamin E concentrate (≈80%) from groundnut oil was used. The results are shown in Table 9.

TABLE 9

Isolation of Vitamin E Isomers (α-T, β-T, γ-T and δ-T) from Groundnut Oil

| Fractions | Collection Time (mm) | Vit. E α-T | Vit. E α-T$_3$ | Vit. E γ-T$_3$ | Vit. E δ-T$_3$ |
|---|---|---|---|---|---|
| S/M | — | 42.9 | 1.5 | 34.4 | 3 |
| 1 | — | — | — | — | — |
| 2 | 35–41 | 100 | — | — | — |

TABLE 9-continued

Isolation of Vitamin E Isomers (α-T, β-T, γ-T and δ-T) from Groundnut Oil

| Fractions | Collection Time (mm) | Vit. E α-T | Vit. E α-T$_3$ | Vit. E γ-T$_3$ | Vit. E δ-T$_3$ |
|---|---|---|---|---|---|
| 3 | 42–47 | — | 80 | — | — |
| 4 | 48–55 | — | — | 100 | — |
| 5 | 58–65 | — | — | — | 85 |

Example 10

The procedure of example 1 was repeated except that a vitamin E concentrate (≈80%) from rice bran oil was used. The results are shown in Table 10.

TABLE 10

Isolation of Vitamin E Isomers (αT, β-T, γ-T and δT) from Rice bran Oil

| Fractions | Collection Time (mm) | Vit. E α-T | Vit. E α-T$_3$ | Vit. E γ-T$_3$ | Vit. E δ-T$_3$ |
|---|---|---|---|---|---|
| S/M | — | 28.2 | 5 | 20.6 | 38.5 |
| 1 | — | — | — | — | — |
| 2 | 35–41 | 100 | — | — | — |
| 3 | 42–47 | — | 85 | — | — |
| 4 | 48–55 | — | — | 100 | — |
| 5 | 58–65 | — | — | — | 100 |

Example 11

The procedure of example 1 was repeated except that a vitamin E concentrate (≈80%) from sunflower seed oil was used. The results are shown in Table 11.

TABLE 11

Isolation of Vitamin E Isomers (α-T, β-T, γ-T and δ-T) from Sunflower Seed Oil

| Fractions | Collection Time (min) | Vit. E α-T | Vit. E β-T | Vit. E γ-T | Vit. E δ-T |
|---|---|---|---|---|---|
| S/M | — | 80.8 | 3.3 | 1.1 | — |
| 1 | — | — | — | — | — |
| 2 | 35–41 | 100 | — | — | — |
| 3 | 42–47 | — | 85 | — | — |
| 4 | 48–55 | — | — | 85 | — |
| 5 | 58–65 | — | — | — | — |

Example 12

The procedure of example 1 was repeated except that a C-18 reverse phase silica gel was used as the adsorbent, the pressure was 180 kg/cm$^2$, and the CO$_2$: ethanol ratio was 93.75%: 6.25%. Four vitamin E isomers (alpha-tocopherol, alpha-tocotrienol, gamma-tocotrienol, and delta-tocotrienol) were eluted in the same elution order as in example 1 and collected in high purity as in example 1. The same procedures, using a C-18 reverse phase silica gel as the adsorbent, was repeated for the other palm oil products, palm oil by-products, and vegetable oils mentioned in examples 2–11. Similar elution order for the vitamin E isomers was for the C-18 reverse phase silica gel as was observed for the silica gel.

What is claimed is:

1. A method for separating vitamin E isomers from a vegetable oil comprising:

(a) esterifying free fatty acid components of the vegetable oil, or trans-esterifying glyceride components of the vegetable oil, with one or more monohydric alcohols to provide esters;

(b) removing the esters to provide a vitamin E concentrate;

(c) combining the vitamin E concentrate with an adsorbent to effect adsorption of the vitamin E isomers on the adsorbent; and (d) selectively desorbing the vitamin E isomers from the adsorbent with a solvent under supercritical conditions.

2. The method of claim 1, wherein the vitamin E isomers are one or more of α-tocopherol, β-tocopherol, γ-tocopherol, δ-tocopherol, α-tocotrienol, β-tocotrienol, γ-tocotrienol and δ-tocotrienol.

3. The method of claim 1, wherein the adsorbent is selected from the group consisting of silica gel, reverse phase C-18 silica gel, and mixtures thereof.

4. The method of claim 1, wherein the solvent is selected from the group consisting of carbon dioxide, propane, propene, and ethylene.

5. The method of claim 1, wherein the separation is performed at a temperature of about 30–1000° C. and a pressure of about 50–600 kg/cm$^2$.

6. The method of claim 1, wherein the alcohol is $C_1$ to $C_8$ alcohol.

7. The method of claim 1, wherein: the esterification is carried out by employing one or more catalysts selected from the group consisting of a solid alkali metal bisulfate, a sulfate acid, a strongly acidic-ion exchange resin and an enzyme; and the trans-esterification is carried out by employing one or more catalysts selected from a group consisting of a basic catalyst and an enzyme.

8. The method of claim 1, wherein the desorbing step occurs at an operating temperature and an operating pressure that is substantially constant throughout the desorbing step.

9. The method of claim 1, wherein the desorbing involves using a combination of a solvent and an entrainer.

10. The method of claim 9, wherein the entrainer comprises an alkyl alcohol.

11. The method of claim 1, wherein the esters are removed using vacuum distillation.

12. The method of claim 1, wherein the vegetable oil is selected from the group consisting of palm oil, corn oil, rapeseed oil, olive oil, cottonseed oil, rice bran oil, soyabean oil, groundnut oil, and sunflower oil.

13. A method for separating vitamin E isomers from a vegetable oil comprising:

(a) esterifying free fatty acid components of the vegetable oil, or trans-esterifying glyceride components of the vegetable oil, with one or more monohydric alcohols to provide esters;

(b) removing the esters to provide a vitamin E concentrate;

(c) combining the vitamin E concentrate with an adsorbent to effect adsorption of the vitamin E isomers on the adsorbent; and (d) selectively desorbing the vitamin E isomers from the adsorbent with a solvent under supercritical conditions; wherein the solvent comprises an ethanol entrainer.

14. The method of claim 13, wherein the vitamin E isomers are one or more of α-tocopherol, β-tocopherol, γ-tocopherol, δ-tocopherol, α-tocotrienol, β-tocotrienol, γ-tocotrienol and δ-tocotrienol.

15. The method of claim 13, wherein the adsorbent is selected from the group consisting of silica gel, reverse phase C-18 silica gel, and mixtures thereof.

16. The method of claim 13, wherein the solvent is selected from the group consisting of carbon dioxide, propane, propene, and ethylene.

17. The method of claim 13, the separation is performed at a temperature of about 30–1000° C. and a pressure of about 50–600 kg/cm$^2$.

18. The method of claim 13, wherein the alcohol is $C_1$ to $C_8$ alcohol.

19. The method of claim 13, wherein the esterification is carried out by employing one or more catalysts selected from the group consisting of a solid alkali metal bisulfate, a sulfate acid, a strongly acidic-ion exchange resin and an enzyme; and the trans-esterification is carried out by employing one or more catalysts selected from the group consisting of a basic catalyst and/or an enzyme.

20. The method of claim 13, wherein the desorbing step occurs at an operating temperature and an operating pressure that is substantially constant throughout the desorbing step.

21. The method of claim 13, wherein the vegetable oil is selected from the group consisting of palm oil, corn oil, rapeseed oil, olive oil, cottonseed oil, rice bran oil, soyabean oil, groundnut oil, and sunflower oil.

22. The method of claim 1 or 13, wherein the method further comprises saponifying the vitamin E concentrate obtained from step (b) to provide saponified products and removing the saponified products from the vitamin E concentrate prior to step (c).

* * * * *

UNITED STATES PATENT AND TRADEMARK OFFICE
CERTIFICATE OF CORRECTION

PATENT NO.    : 6,656,358 B2
DATED         : December 2, 2003
INVENTOR(S)   : Choo Yuen May, Ma Ah Ngan and Yusof Basiron It is certified that error appears in the above-identified patent and that said Letters Patent is hereby corrected as shown below:

Column 9,
Line 23, replace "30-1000° C." with -- 30-100° C. --

Column 10,
Line 24, replace "30-1000° C." with -- 30-100° C. --

Signed and Sealed this

Ninth Day of March, 2004

JON W. DUDAS
*Acting Director of the United States Patent and Trademark Office*